United States Patent
Lee et al.

(10) Patent No.: US 9,362,096 B2
(45) Date of Patent: Jun. 7, 2016

(54) COMBUSTION PRETREATMENT-ISOTOPE DILUTION MASS SPECTROMETRY

(71) Applicant: KOREA RESEARCH INSTITUTE OF STANDARDS AND SCIENCE, Daejeon (KR)

(72) Inventors: Kyoung-Seok Lee, Daejeon (KR); In Jung Kim, Daejeon (KR); Sung-Pil Jo, Mokpo-si (KR); Hyung Sik Min, Daejeon (KR); Yong Hyeon Yim, Daejeon (KR); Joung Hae Lee, Daejeon (KR); Eui Jin Hwang, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 14/655,845

(22) PCT Filed: Dec. 26, 2013

(86) PCT No.: PCT/KR2013/012191
§ 371 (c)(1),
(2) Date: Jun. 26, 2015

(87) PCT Pub. No.: WO2014/104749
PCT Pub. Date: Jul. 3, 2014

(65) Prior Publication Data
US 2015/0348768 A1    Dec. 3, 2015

(30) Foreign Application Priority Data

Dec. 26, 2012  (KR) .................. 10-2012-0153973

(51) Int. Cl.
| | |
|---|---|
| *H01J 49/04* | (2006.01) |
| *G01N 27/62* | (2006.01) |
| *G01N 27/70* | (2006.01) |
| *H01J 49/00* | (2006.01) |

(52) U.S. Cl.
CPC ............ *H01J 49/0422* (2013.01); *G01N 27/62* (2013.01); *G01N 27/70* (2013.01); *H01J 49/00* (2013.01)

(58) Field of Classification Search
USPC .......................................... 250/288, 282, 281
See application file for complete search history.

(56) References Cited

U.S. PATENT DOCUMENTS 4,950,456 A * 8/1990 Forster .................. G01N 31/12
261/76

FOREIGN PATENT DOCUMENTS

| JP | 2008070134 A | 3/2008 |
| JP | 2008535170 A | 8/2008 |
| KR | 100654293 B1 | 12/2006 |

OTHER PUBLICATIONS

Nam, K. et al., "Microwave-Induced Combustion for ICP-MS: A Generic Approach to Trace Elemental Analyses of Pharmaceutical Products," Spectroscopy, vol. 26, No. 4, Apr. 2011, 5 pages.
(Continued)

*Primary Examiner* — Kiet T Nguyen
(74) *Attorney, Agent, or Firm* — Alleman Hall McCoy Russell & Tuttle LLP

(57) ABSTRACT

Provided is a combustion pretreatment-isotope dilution mass spectrometry measuring concentration of a target element for detection contained in a target sample for detection by using an isotope dilution mass spectrometry, including: pretreating the target sample for detection by combustion during an isotope dilution mass spectrometry, to thereby stabilize an isotope and further improve analysis ability, and therefore, the present invention is expected to be utilized as an element analysis method surpassing accuracy of the existing mass spectrometry method.

14 Claims, 2 Drawing Sheets

(56) References Cited

OTHER PUBLICATIONS

Pereira, J. et al., "Evaluation of Sample Preparation Methods for Polymer Digestion and Trace Elements Determination by ICPMS and ICPOES," J. Anal. At. Spectrom., vol. 26, No. 9, Jun. 2011, 9 pages.

ISA Korean Intellectual Property Office, International Search Report Issued in Application No. PCT/KR2013/012191, Mar. 11, 2014, WIPO, 5 pages.

\* cited by examiner

COMBUSTION PRETREATMENT-ISOTOPE DILUTION MASS SPECTROMETRY

CROSS REFERENCE TO RELATED APPLICATIONS

The present application is a U.S. National Phase of International Patent Application Serial No. PCT/KR2013/012191, entitled "COMBUSTION PRETREATMENT-ISOTOPE DILUTION MASS SPECTROMETRY," filed on Dec. 26, 2013, which claims priority to Korean Patent Application No. 10-2012-0153973, entitled "COMBUSTION PRETREATMENT-ISOTOPE DILUTION MASS SPECTROMETRY," filed on Dec. 26, 2012, the entire contents of each of which are hereby incorporated by reference for all purposes.

TECHNICAL FIELD

The present invention relates to combustion pretreatment-isotope dilution mass spectrometry as a method for measuring the concentration of an element to be detected contained in a sample to be detected by using isotope dilution mass spectrometry, including a step of pretreating the sample to be detected by combusting the same during isotope dilution mass spectrometry. The present invention stabilizes an isotope and improves analysis ability, and thus is expected to be used as an element analysis method surpassing the accuracy of an existing mass analysis method.

BACKGROUND ART

A method of analyzing elements configuring a material has already been researched and developed over a long time in one field of chemistry, which is referred to as analytical chemistry, in addition to methods of quantifying elements by a number of analysis methods and analysis apparatuses.

As a quantification method for an element which has been currently and mainly used, there are fluorescence spectroscopy, atomic absorption spectroscopy (AAS), X-ray fluorescence (XRF), inductively coupled plasma-atomic emission spectrometry (ICP-AES), instrumental neutron activation analysis (INAA), and the like. In describing the various methods below, the AAS has a relatively slow analysis speed, and may be seriously disturbed by medium since it is not capable of performing a multi-element simultaneous analysis. The ICP-AES is capable of detecting multi-elements at the same time, analyzing most of the elements at a sensitivity of about tens of μg/kg (ppb), but has relatively severe spectral interference. The XRF is capable of analyzing many elements at the same time and is possible to perform non-destructive analysis in a case of a metal sample or a powder sample, but merely has a detection limit in a unit of about mg/kg (ppm). The INNA has advantages in that sensitivity is high and multi-element simultaneous analysis by a non-destructive method is possibly performed, but has a disadvantage in that it is difficult to be used since a large size of neutron source such as a nuclear reactor and radiation detection apparatuses are required.

The ICP-MS is capable of rapidly and accurately analyzing elements present in a liquid sample up to a level of μg/kg (ppb) to ng/kg (ppt), and has a high sensitivity and a large range for quantification. In addition, since measurement for an isotope ratio is possible, an isotope dilution method may be applied. The isotope dilution method has been used as an analysis method for a trace component in a biological field, an environmental engineering field, a nuclear energy field, and the like. Korean Patent No. 10-0654293 (Patent Document 1) discloses a specialized isotope dilution mass spectrometry of reactive species.

Since isotopes have different mass only, but almost the same physical and chemical properties, they are used as the best internal standard material in analysis of a trace component. Therefore, when enriched stable isotopes with a known amount with respect to an element to be analyzed are put into a sample to allow equilibrium among the isotopes, and then a ratio of the isotopes is measured, quantification is possibly performed regardless of loss in elements to be measured which easily occurs during pretreatment for the target sample for detection. In addition, since a medium effect involved in an analysis process also equally affects, all isotopes, an effect by the medium components on the measurement of the ratio of the isotopes may be reduced under an assumption in which complete equilibrium is achieved. The isotope dilution method may obtain significantly accurate analysis results on elements having two or more stable isotopes to be mainly used for determination of certified values of a certified standard material.

The ICP-MS is a method of high temperature-plasma spraying a sample solution obtained by pretreatment to break up to an atomic unit, followed by ionization, and separation according to difference in mass to charge ratio of ions, to measure a size of ion signal. In the ICP-MS, even though considerable time and effort are required for pretreatment for the target sample, 20 kinds or more of elements are capable of being simultaneously measured, and detection limit of the device is significantly low, such that traces of harmful elements present in the sample are possibly measured, and stable measurement values in view of reproducibility and reliability of the measurement values are provided as compared to the other existing measurement methods. However, to do this, significantly considerable efforts are needed in the pretreatment of the sample. The pretreatment of the sample for ICP-MS measurement mainly uses an acid decomposition including a heating process by using strong acid, wherein different kinds of acids and optimized heating time are required for each sample. For example, in a case of a plastic sample, or the like, which is difficult to decompose, several hours or more of heating time using dangerous concentrated nitric acid and concentrated sulfuric acid are required in some cases. In this process, due to incomplete decomposition of the sample or remaining sulfuric acid, spray efficiency of the sample solution is not good, which causes a negative influence on the measurement results. In addition, in volatile elements such as arsenic (As), bromine (Br), chlorine (Cl), and the like, loss in the pretreatment commonly happens, and possibility of pollution during the pretreatment over a long period of time increases, which causes distortion of the measurement results. In order to solve the above-described problems, various researches on the pretreatment method of the sample are required together with methods for increasing accuracy of an inductively coupled plasma mass spectrometry.

DISCLOSURE

Technical Problem

An object of the present invention is to provide an element analysis method capable of increasing efficiency of pretreatment and decreasing uncertainty in measurement to obtain more accurate measurement results.

Technical Solution

In one general aspect, there is provided a combustion pretreatment-isotope dilution inductively coupled plasma mass spectrometry (combustion-ID-ICP/MS) (hereinafter, referred to as a combustion pretreatment-isotope dilution mass spectrometry) measuring concentration of a target element for detection contained in a target sample for detection by using an isotope dilution inductively coupled plasma mass spectrometry, the combustion pretreatment-isotope dilution mass spectrometry (combustion-ID-ICP/MS) including: pretreating the target sample for detection by combustion during an isotope dilution mass spectrometry.

The combustion pretreatment-isotope dilution mass spectrometry may include: a) performing an inductively coupled plasma-mass spectrometry on a first standard solution containing a reference isotope and an enriched isotope each at a predetermined amount, the reference isotope and the enriched isotope being isotopes of the target element for detection, to measure an isotope ratio between the reference isotope and the enriched isotope of the first standard solution; b) performing an inductively coupled plasma-mass spectrometry on a combusted material obtained by combusting the target sample for detection to measure an isotope ratio between a reference isotope and an enriched isotope contained in the target sample for detection; c) performing an inductively coupled plasma-mass spectrometry on a combusted material obtained by combusting a first mixed solution prepared by uniformly mixing the first standard solution with the target sample for detection to measure an isotope ratio between a reference isotope and an enriched isotope contained in the first mixed solution; and d) calculating concentration of the target element for detection contained in the target sample for detection by using the isotope ratios from a), b), and c).

The target element for detection may be any one or two or more selected from the group consisting of Cl, Br, Cd, Pb, Hg, Se, Li, B, Mg, Si, S, K, Ca, Ti, V, Cr, Fe, Ni, Cu, Zn, Ga, Ge, Rb, Sr, Zr, Mo, Ru, Pd, Ag, In, Sn, Sb, Te, Cs, Ba, Ce, Nd, Sm, Eu, Gd, Dy, Er, Yb, Hf, Ta, W, Re, Os, Ir, Pt, Tl, and U.

The combustion of each of b) and c) may be a pretreatment process of performing complete combustion at 900° C. to 1200° C. for 10 minutes to 60 minutes to obtain the combusted material.

The pretreatment process may include injecting an additive for complete combustion, collecting the combusted material in an absorbent solution, and adsorption-removing an organic material, and the target sample for detection may be completely combusted to be a gaseous state by the pretreatment process.

The additive for complete combustion may be one or two or more selected from the group consisting of vanadium oxide, iron oxide, permanganate, chromate, osmium tetroxide, and perchlorate, and the additive may be injected to promote combustion.

The absorbent solution may be one or two or more selected from the group consisting of deionized water, sodium hydroxide, tetramethylammonium hydroxide, ammonium carbonate, and hydrogen peroxide, and the absorbent solution may be used to collect the combusted material.

In addition, the adsorption-removing of the organic material may be a step of removing the organic material by using one or two or more adsorbents selected from the group consisting of deionized water, sodium hydroxide, tetramethylammonium hydroxide, ammonium carbonate, and hydrogen peroxide.

The combustion pretreatment-isotope dilution mass spectrometry may include: i) performing an inductively coupled plasma-mass spectrometry on a second standard solution containing a reference isotope and an enriched isotope each at a predetermined amount, the reference isotope and the enriched isotope being isotopes of the target element for detection; and on a third standard solution containing a reference isotope and an enriched isotope each at a predetermined amount at a concentration which is different from that of the second standard solution, the reference isotope and the enriched isotope being isotopes of the target element for detection, to measure an isotope ratio between the reference isotope and the enriched isotope, of each of the second standard solution and the third standard solution; ii) performing an inductively coupled plasma-mass spectrometry on a combusted material obtained by combusting the target sample for detection to measure an isotope ratio between a reference isotope and an enriched isotope contained in the target sample for detection; iii) performing an inductively coupled plasma-mass spectrometry on a combusted material obtained by combusting a second mixed solution prepared by uniformly mixing the second standard solution with the target sample for detection, and on a combusted material obtained by combusting a third mixed solution prepared by uniformly mixing the third standard solution with the second standard solution, to measure an isotope ratio between a reference isotope and an enriched isotope contained in each of the second mixed solution and the third mixed solution; and iv) calculating concentration of the target element for detection contained in the target sample for detection by using the isotope ratios from i), ii), and iii).

The combustion of each of ii) and iii) may be a pretreatment process of performing complete combustion at 900° C. to 1200° C. for 10 minutes to 60 minutes to obtain the combusted material.

The second standard solution may contain the enriched isotope of the target element for detection at a concentration higher than that of the third standard solution.

Here, the pretreatment process may include adding an additive for complete combustion, collecting the combusted material in an absorbent solution, and adsorption-removing an organic material.

The additive for complete combustion may be one or two or more selected from the group consisting of vanadium oxide, iron oxide, permanganate, chromate, osmium tetroxide, and perchlorate, and the additive may be added to promote combustion.

The absorbent solution may be one or two or more selected from the group consisting of deionized water, sodium hydroxide, tetramethylammonium hydroxide, ammonium carbonate, and hydrogen peroxide, and the absorbent solution may be used to collect the combusted material.

In addition, the adsorption-removing of the organic material may be a step of removing the organic material by using one or two or more adsorbents selected from the group consisting of deionized water, sodium hydroxide, tetramethylammonium hydroxide, ammonium carbonate, and hydrogen peroxide.

Advantageous Effects

The combustion pretreatment-isotope dilution mass spectrometry according to the present invention is remarkable in that an isotope dilution inductively coupled plasma mass spectrometry is coupled with a combustion pretreatment, and may overcome disadvantages of the existing pretreatment and general inductively coupled plasma mass spectrometry, such as impossibility of obtaining accurate and reproducible results. In addition, there is provided a novel top level measurement which provides comparable results as INAA, which is one of top level measurements, that is, the same accuracy as INAA and low uncertainty.

Further, the combustion pretreatment in which pretreatment is performed by using combustion may be introduced into the isotope dilution plasma mass spectrometry to minimize problems during the pretreatment process, such as loss, pollution, and the like, and measurement of a concentration may be converted by measurement of an isotope ratio to decrease uncertainty caused by variability of apparatuses in a measurement process, such as change of spray efficiency, shaking of plasma, and the like, thereby further improving analysis ability, such that the present invention is expected to be utilized as an element analysis method surpassing accuracy of the existing mass spectrometry method.

BEST MODE

Figure 1:
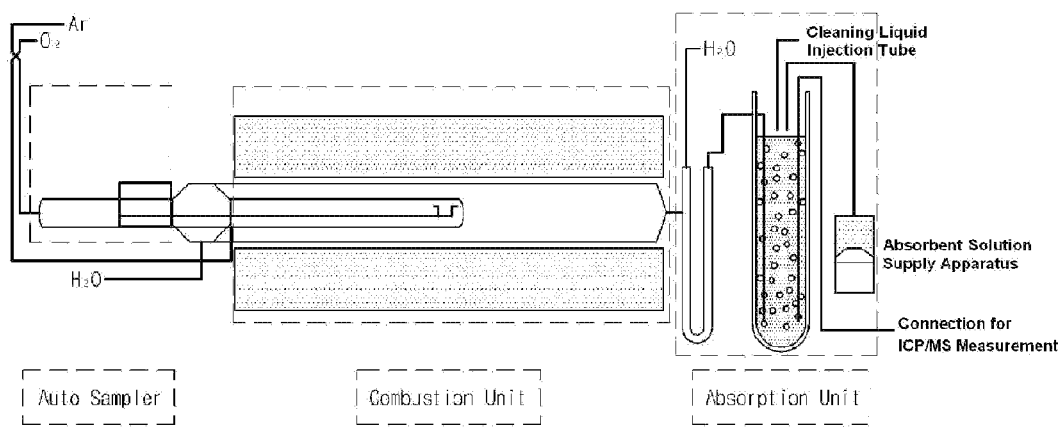
FIG. 1 shows an apparatus for combustion pretreatment, according to the present invention.

Hereinafter, the present invention will be described in detail.

The present invention is directed to providing a combustion pretreatment-isotope dilution inductively coupled plasma mass spectrometry (combustion-ID-ICP/MS). The present inventors developed an element analysis method capable of obtaining more accurate measurement results by measuring content using an isotope dilution mass spectrometry instead of using an ion chromatography method in the existing combustion pretreatment-ion chromatography, and completed the present invention.

The present invention provides a combustion pretreatment-isotope dilution mass spectrometry measuring a concentration of a target element for detection contained in a target sample for detection by using an isotope dilution mass spectrometry, the combustion pretreatment-isotope dilution mass spectrometry, including: pretreating the target sample for detection by combustion during an isotope dilution mass spectrometry.

The target element for detection may be any one or two or more selected from the group consisting of Cl, Br, Cd, Pb, Hg, Se, Li, B, Mg, Si, S, K, Ca, Ti, V, Cr, Fe, Ni, Cu, Zn, Ga, Ge, Rb, Sr, Zr, Mo, Ru, Pd, Ag, In, Sn, Sb, Te, Cs, Ba, Ce, Nd, Sm, Eu, Gd, Dy, Er, Yb, Hf, Ta, W, Re, Os, Ir, Pt, Tl, and U, but the present invention is not limited thereto.

The target sample for detection in the present invention is not significantly limited, but samples that are difficult to be acid decomposition pretreated, such as plastic, nano particles, soil, or the like, may also be detected.

Specifically, according to an exemplary embodiment of the present invention, there is provided a combustion pretreatment-isotope dilution mass spectrometry including:

a) performing an inductively coupled plasma-mass spectrometry on the first standard solution containing a reference isotope and an enriched isotope each at a predetermined amount, the reference isotope and the enriched isotope being isotopes of the target element for detection to measure an isotope ratio between the reference isotope and the enriched isotope of the first standard solution;

b) performing an inductively coupled plasma-mass spectrometry on a combusted material obtained by combusting the target sample for detection to measure an isotope ratio between a reference isotope and an enriched isotope contained in the target sample for detection;

c) performing an inductively coupled plasma-mass spectrometry on a combusted material obtained by combusting a first mixed solution prepared by uniformly mixing the first standard solution with the target sample for detection to measure an isotope ratio between a reference isotope and an enriched isotope contained in the first mixed solution; and d) calculating concentration of the target element for detection contained in the target sample for detection by using the isotope ratios from a), b), and c).

Each step of the present invention is described in more detail.

First, the present invention corresponds to an isotope dilution method, and inductively coupled plasma mass spectrometry (ICP-MS) is capable of measuring an isotope ratio, such that the isotope dilution method may be applied to the ICP-MS. The isotope dilution method is a method in which enriched isotopes of which isotope ratios are known are put into a target sample for detection to allow equilibrium between the isotopes of target element for analysis present in the sample and the added isotopes, and then a changed ratio of the isotopes is measured by using a mass spectrometer to calculate concentration of the element.

Step a) is a step of performing an inductively coupled plasma-mass spectrometry on the first standard solution containing the reference isotope and the enriched isotope each at a predetermined amount, the reference isotope and the enriched isotope being isotopes of the target element for detection, to measure an isotope ratio between the reference isotope and the enriched isotope of the first standard solution.

In order to apply an isotope dilution mass spectrometry (IDMS), it is required to select an enriched isotope and a reference isotope, which is another isotope. Here, isotopes for measurement need to be selected in consideration of an interfering ion. An element without the interfering ion is selected as the reference isotope, and an isotope having the second highest natural abundance ratio after the reference isotope is used as the enriched isotope; however, other isotopes having a low natural abundance ratio may be selected as the enriched isotope. An isotope ratio of the selected enriched isotope/reference isotope or the selected reference isotope/enriched isotope is measured to apply the isotope dilution method.

Here, the first standard solution is a mixed solution containing a large amount of enriched isotopes, and it is preferable as a concentration of the enriched isotope becomes increased, and in general, a material or a solution containing 90%(w/w) or more, specifically, 90 to 99%(w/w) of the enriched isotope is prepared as a solution with a desired concentration to be used.

In step a), the inductively coupled plasma-mass spectrometry is performed on the first standard solution containing the reference isotope and the concentrated isotope as determined above, each at a predetermined amount, to measure an isotope ratio between the reference isotope and the enriched isotope of the first standard solution.

Next, step b) is a step of performing an inductively coupled plasma-mass spectrometry on a combusted material obtained by combusting the target sample for detection to measure an isotope ratio between a reference isotope and an enriched isotope contained in the target sample for detection.

The target sample for detection contains the reference isotope and the enriched isotope selected from step a), each at a predetermined amount, generally being present in a natural abundance ratio. Accordingly, the isotope ratio of the reference isotope and the enriched isotope in step b) may use the known natural abundance ratio without performing direct measurement, such that step b) may be omitted. However, in a case of an element having a large scope of the known isotope natural abundance ratio of the target element for detection or having a large value of uncertainty, it is preferable to directly measure the isotope ratio of the target sample for detection for a more accurate measurement.

In step b), an inductively coupled plasma-mass spectrometry is performed on the combusted material obtained by combustion pretreatment of the target sample for detection to measure an isotope ratio between the reference isotope and the enriched isotope. The combustion pretreatment is described in step c) below in more detail.

Next, step c) is described. Step c) is a step of performing an inductively coupled plasma-mass spectrometry on a combusted material obtained by combusting a first mixed solution prepared by uniformly mixing the first standard solution with the target sample for detection to measure an isotope ratio between a reference isotope and an enriched isotope contained in the first mixed solution.

The present inventors introduced the existing technology of combustion pretreatment-ion chromatography pretreatment method into the isotope dilution mass spectrometry of the present invention, found that the introduction of the combustion pretreatment process is capable of reducing an error occurring in pretreatment process which is a disadvantage of an inductively coupled plasma mass spectrometry, and further increasing accuracy of the existing mass spectrometry, and completed the present invention.

Here, an amount in which the first standard solution is added to the target sample for detection may vary according to the target element for detection and may vary according to the concentration and the isotope ratio of the first standard solution. The first standard solution may be added so that the isotope ratio of the enriched isotope/the reference isotope in the prepared first mixed solution is 0.3 to 5, but the present invention is not necessarily limited thereto. When it is out of the above-described range, distortion may occur in the measurement of the isotope ratio to increase uncertainty.

The first mixed solution as prepared above is subjected to the pretreatment process by combustion, that is, the combustion pretreatment process, which is similar to step b), wherein combustion in steps b) and c) are preferably performed under gas atmosphere such as oxygen, argon, or the like, at a temperature of 900° C. to 1200° C. for 10 minutes to 60 minutes. When the combustion is performed at less than 900° C., incomplete combustion may occur, and when the combustion is performed at more than 1200° C., a combustion unit may be overheated. In addition, when the combustion is performed for less than 10 minutes, incomplete combustion may also occur, and 60 minutes or more are permissible as time for combustion; however, time efficiency of the pretreatment process needs to be considered.

The inductively coupled plasma-mass spectrometry is performed on the combusted material obtained by the combustion pretreatment as described above to measure the isotope ratio between the reference isotope and the enriched isotope contained in the first mixed solution.

The pretreatment process may include injecting an additive for complete combustion, collecting the combusted material in an absorbent solution, and adsorption-removing an organic material.

In a process of preparing the sample for combustion, a step of injecting an additive may be performed so as to favorably perform the combustion, wherein the additive for complete combustion may be one or two or more selected from the group consisting of vanadium oxide, iron oxide, permanganate, chromate, osmium tetroxide, and perchlorate, and the additive may be added to promote combustion.

Then, the step of collecting the final sample combusted material obtained by the combustion as described above is performed, wherein the final sample combusted material is collected by an absorbent solution. The absorbent solution may be one or two or more selected from the group consisting of deionized water, sodium hydroxide, tetramethylammonium hydroxide, ammonium carbonate, and hydrogen peroxide, and the absorbent solution may be used to collect the combusted material.

In addition, the step of adsorption-removing the organic material remaining in a combustion tube, and the like, immediately after the combustion, may be added, and in the adsorption-removing step, the organic material may be removed by using one or two or more adsorbents selected from the group consisting of deionized water, sodium hydroxide, tetramethylammonium hydroxide, ammonium carbonate, and hydrogen peroxide. The adsorption-removing step may be omitted if the combustion is completely performed, and it is considered as a kind of a cleaning step.

The inductively coupled plasma mass spectrometry included in steps a), b), and c) may be performed by general methods. Briefly, the target sample for detection is firstly sprayed and supplied in a gaseous state, and gas of the target sample for detection injected into a plasma is decomposed in plasma into atoms and ionized. The ions produced as above are separated by mass difference to detect respective isotope ions, thereby making it possible to measure the isotope ratio between the reference isotope and the enriched isotope. Oxygen gas is supplied to the gas of the target sample for detection according to the target element for detection to generate ions on oxides of the target element for detection, and the ions on the oxides are separated by mass difference, and detected, thereby making it possible to measure the isotope ratio between the reference isotope and the enriched isotope.

Then, step d) is a step of calculating concentration of the target element for detection contained in the target sample for detection by using the isotope ratios from a), b), and c).

Here, in step d), concentration of the target element for detection contained in the target sample for detection may be calculated by Equation 1 below:

$$c_x = c_y \times \frac{m_y}{w \times m_x} \times \frac{R_y - R_b}{R_b - R_x} \times \frac{\sum R_{xi}}{\sum R_{yi}} - c_{blank} \qquad \text{[Equation 1]}$$

in Equation 1 above, subscript x is a target sample for detection, subscript y is a first standard solution, and subscript b is a first mixed solution, $c_x$: Concentration of target element for detection contained in target sample for detection, $c_y$: Concentration of target element for detection contained in first standard solution, $m_x$: Mass of target sample for detection, $m_y$: Mass of first standard solution added together with target sample for detection for preparation of first mixed solution, w: Dry mass correction factor, $R_x$: Isotope ratio between reference isotope and enriched isotope of target sample for detection, $R_y$: Isotope ratio between reference isotope and enriched isotope of first standard solution $R_b$: Isotope ratio between reference isotope and enriched isotope of first mixed solution, $\Sigma R_{xi}$: Sum of abundance ratios of isotopes to reference isotope, from each isotope of target element for detection in target sample for detection, $\Sigma R_{yi}$: Sum of abundances ratios of isotopes to reference isotope, from each isotope of target element for detection in first standard solution, and $c_{blank}$: Concentration of blank sample for checking measurement procedure.

The dry mass correction factor in Equation 1 above means a factor which converts into a concentration with respect to dry mass according to humidity environment and sample, and the blank sample for checking measurement procedure is a solution obtained by injecting a standard solution only, excepting for the target sample for detection at the time of preparing the first mixed solution in step c), and then performing the same combustion process, which is prepared to check problems such as pollution, and the like.

This method may be applied to the first standard solution having the enriched isotope in which both of the concentration and the isotope abundance ratio have measurement traceability in a measurement unit set by the SI international unit system, and since the first standard solution serves as a standard solution, quantification of the target element for detection is possible with only the isotope abundance ratio of the first standard solution and the target sample for detection.

Meanwhile, according to another exemplary embodiment of the present invention, there is provided a combustion pretreatment-isotope dilution mass spectrometry including:

i) performing an inductively coupled plasma-mass spectrometry on a second standard solution containing a reference isotope and an enriched isotope each at a predetermined amount, the reference isotope and the enriched isotope being isotopes of the target element for detection; and on a third standard solution containing a reference isotope and an enriched isotope each at a predetermined amount at a concentration which is different from that of the second standard solution, the reference isotope and the enriched isotope being isotopes of the target element for detection, to measure an isotope ratio between the reference isotope and the enriched isotope, of each of the second standard solution and the third standard solution;

ii) performing an inductively coupled plasma-mass spectrometry on a combusted material obtained by combusting the target sample for detection to measure an isotope ratio between a reference isotope and an enriched isotope contained in the target sample for detection;

iii) performing an inductively coupled plasma-mass spectrometry on a combusted material obtained by combusting a second mixed solution prepared by uniformly mixing the second standard solution with the target sample for detection, and on a combusted material obtained by combusting a third mixed solution prepared by uniformly mixing the third standard solution with the second standard solution, to measure an isotope ratio between a reference isotope and an enriched isotope contained in each of the second mixed solution and the third mixed solution; and iv) calculating concentration of the target element for detection contained in the target sample for detection by using the isotope ratios from i), ii), and iii).

First, the present invention corresponds to an isotope dilution method, and inductively coupled plasma mass spectrometry (ICP-MS) is capable of measuring an isotope ratio, such that the isotope dilution method may be applied to the ICP-MS. The isotope dilution method is a method in which enriched isotopes (spikes) of which isotope ratios are known are put into a target sample for detection to allow equilibrium between the isotopes of target element for analysis present in the sample and the added isotopes, and then a changed ratio of the isotopes is measured by using a mass spectrometer to calculate concentration of the element.

The method according to another exemplary embodiment of the present invention may be applied to a case where in the enriched isotope of the second standard solution, the isotope abundance ratio is generally known, but there is no accurate concentration with certified values, and the isotope ratio between the reference isotope and the enriched isotope of the second mixed solution consisting of the target sample for detection-the second standard solution, and the isotope ratio between the reference isotope and the enriched isotope of the third mixed solution consisting of third standard solution-the second standard solution, which are mediated by the second standard solution, are double-related to each other, and therefore, it is referred to as "double IDMS".

Each step of the present invention is described in more detail.

Step i) is a step of performing an inductively coupled plasma-mass spectrometry on a second standard solution containing a reference isotope and an enriched isotope each at a predetermined amount, the reference isotope and the enriched isotope being isotopes of the target element for detection; and on a third standard solution containing a reference isotope and an enriched isotope each at a predetermined amount at a concentration which is different from that of the second standard solution, the reference isotope and the enriched isotope being isotopes of the target element for detection, to measure an isotope ratio between the reference isotope and the enriched isotope, of each of the second standard solution and the third standard solution.

In order to apply an isotope dilution mass spectrometry (ID-MS), it is required to select an enriched isotope and a reference isotope which is another isotope. Here, isotopes for measurement need to be selected in consideration of an interfering ion. The isotope dilution method may be applied by selecting an element without the interfering ion as the reference isotope, and using an isotope having the second highest natural abundance ratio after the reference isotope as the enriched isotope, to measure the isotope ratio between the reference isotope/the enriched isotope, and according to the target element for detection, other stable isotopes except for an element having the second smallest abundance ratio after the reference isotope may be selected as the enriched isotope.

Here, the second standard solution is a mixed solution containing a large amount of enriched isotopes, and it is preferable as a concentration of the enriched isotope becomes increased, and in general, a material or a solution containing 90%(w/w) or more, specifically, 90 to 99.9%(w/w) of the enriched isotope is prepared as a solution with a desired concentration to be used.

The second standard solution preferably contains the isotope of the target element for detection with higher concentration than that of the third standard solution. When the mixed solution is prepared, the usage amount of the standard solution is large, the combustion time is increased, or possibility of incomplete combustion is increased, such that a small amount with high concentration is preferably used, and when the second standard solution has a lower concentration than that of the third standard solution, a large amount of the second standard solution may be used. Therefore, it is preferred that the second standard solution has a higher concentration as compared to the third standard solution, but the present invention is not limited thereto.

The third standard solution is not significantly limited in view of the isotope, but preferably, has an isotope abundance ratio similar to that of the target sample for detection. When both of the third standard solution and the target sample for detection have general isotope natural abundance ratio, the known natural abundance ratio may be used as the isotope ratio between the reference isotope and the enriched isotope of each of the third standard solution and the target sample for detection, without performing direct measurement in i) and ii), such that the steps may be omitted. However, in a case of an element having a large scope of the known isotope natural abundance ratio of the target element for detection or having a large value of uncertainty, it is preferable to directly measure the isotope ratio of the third standard solution and the target sample for detection for a more accurate measurement.

Step i) is a step of performing an inductively coupled plasma-mass spectrometry on the second standard solution and the third standard solution each containing a reference isotope and an enriched isotope as determined above, each at a predetermined amount, to measure the isotope ratio between the reference isotope and the enriched isotope.

Next, step ii) is a step of performing an inductively coupled plasma-mass spectrometry on a combusted material obtained by combusting the target sample for detection to measure an isotope ratio between a reference isotope and an enriched isotope contained in the target sample for detection. When the target sample for detection has the already-known general isotope natural abundance ratio as described above, the direct measurement need not be performed but may be omitted. However, it is preferable to perform direct measurement for more accurate measurement.

Next, step iii) is described. Step iii) is a step of performing an inductively coupled plasma-mass spectrometry on a combusted material obtained by combusting the second mixed solution prepared by uniformly mixing the second standard solution with the target sample for detection, and on a combusted material obtained by combusting the third mixed solution prepared by uniformly mixing the third standard solution with the second standard solution, to measure an isotope ratio between a reference isotope and an enriched isotope contained in each of the second mixed solution and the third mixed solution.

The present inventors introduced the existing technology of combustion pretreatment-ion chromatography pretreatment method into the isotope dilution mass spectrometry of the present invention, and found that the introduction of the combustion pretreatment process is capable of reducing an error occurring in a pretreatment process which is a disadvantage of the inductively coupled plasma mass spectrometry, and further increasing accuracy of the existing mass spectrometry, and completed the present invention.

Here, an amount in which the second standard solution is added to the target sample for detection may vary according to the target element for detection and may vary according to the concentration and the isotope ratio of the second standard solution. However, the second standard solution may be added so that the isotope ratio of the enriched isotope/the reference isotope in the prepared second mixed solution is 0.1 to 10, but the present invention is not necessarily limited thereto. When it is out of the above-described range, distortion may occur in the measurement of the isotope ratio to increase uncertainty.

In addition, an amount of which the second standard solution is added to the third standard solution may vary according to the target element for detection and may vary according to the concentration and the isotope ratio of the second standard solution. However, it is preferable to make the isotope ratio of the enriched isotope/the reference isotope in the prepared third mixed solution to be similar to that of the second mixed solution, for a more accurate measurement of the isotope ratio. However, the present invention is not necessarily limited thereto.

The second mixed solution and the third mixed solution as prepared above are subjected to a pretreatment process by combustion, wherein the combustion is preferably performed at 900° C. to 1200° C. for 10 minutes to 60 minutes. When the combustion is performed at less than 900° C., incomplete combustion may occur, and when the combustion is performed at more than 1200° C., a combustion unit may be overheated. In addition, when the combustion is performed for less than 10 minutes, incomplete combustion may also occur, and 60 minutes or more are permissible as time for combustion; however, time efficiency of the pretreatment process needs to be considered.

Here, since the third mixed solution already has a solution state which is easy to perform the inductively coupled plasma mass spectrometry, such that the combustion pretreatment process may be omitted.

The inductively coupled plasma-mass spectrometry is performed on the combusted material obtained by the combustion pretreatment process as described above to measure the isotope ratio between the reference isotope and the enriched isotope contained in each of the second mixed solution and the third mixed solution.

The pretreatment process may include injecting an additive for complete combustion, collecting the combusted material in an absorbent solution, and adsorption-removing an organic material.

The additive for complete combustion may be one or two or more selected from the group consisting of vanadium oxide, iron oxide, permanganate, chromate, osmium tetroxide, and perchlorate, and the additive may be added to promote combustion.

The absorbent solution may be one or two or more selected from the group consisting of deionized water, sodium hydroxide, tetramethylammonium hydroxide, ammonium carbonate, and hydrogen peroxide, and the absorbent solution may be used to collect the combusted material.

In addition, the adsorption-removing of the organic material may be a step of removing the organic material by using one or two or more adsorbents selected from the group consisting of deionized water, sodium hydroxide, tetramethylammonium hydroxide, ammonium carbonate, and hydrogen peroxide.

The inductively coupled plasma mass spectrometry included in steps i), ii), and iii) may be performed by general methods. Briefly, the target sample for detection is firstly sprayed and supplied in a gaseous state, and gas of the target sample for detection injected into a plasma is decomposed into atoms in plasma and ionized. The ions produced as above are separated by mass difference to detect respective isotope ions, thereby making it possible to measure the isotope ratio between the reference isotope and the enriched isotope. Oxygen gas is supplied to the gas of the target sample for detection according to the target element for detection to generate ions on oxides of the target element for detection, and the ions on the oxides are separated by the mass difference, and detected, thereby making it possible to measure the isotope ratio between the reference isotope and the enriched isotope.

Then, step iv) is a step of calculating concentration of the target element for detection contained in the target sample for detection by using the isotope ratios from i), ii), and iii).

Here, in step iv), concentration of the target element for detection contained in the target sample for detection may be calculated by Equation 2 below:

$$c_x = c_v \times \frac{m_u m_v}{w \times m_x m'_u} \times \frac{R_u - R_{b'}}{R_{b'} - R_x} \times \frac{R_{b''} - R_v}{R_u - R_{b''}} \times \frac{\sum R_{xi}}{\sum R_{vi}} - c_{blank} \quad \text{[Equation 2]}$$

in Equation 2 above, subscript x is a target sample for detection, subscript u is a second standard solution, subscript v is a third standard solution, subscript b' is a second mixed solution, and subscript b" is a third mixed solution, $c_x$: Concentration of element contained in target sample for detection, $c_v$: Concentration of element contained in third standard solution, $m_x$: Mass of target sample for detection, $m_u$: Mass of second standard solution added together with target sample for detection for preparation of second mixed solution $m_v$: Mass of third standard solution used for preparation of third mixed solution, $m'_u$: Mass of second standard solution added together with third standard solution for preparation of third mixed solution w: Dry mass correction factor, $R_x$: Isotope ratio between reference isotope and enriched isotope of target element for detection in target sample for detection $R_u$: Isotope ratio between reference isotope and enriched isotope of second standard solution $R_v$: Isotope ratio between reference isotope and enriched isotope of third standard solution $R_{b'}$: Isotope ratio between reference isotope and enriched isotope of second mixed solution $R_{b''}$: Isotope ratio between reference isotope and enriched isotope of third mixed solution $\Sigma R_{xi}$: Sum of abundance ratios of isotopes to reference isotope from each isotope of target element for detection in target sample for detection $\Sigma R_{vi}$: Sum of abundance ratios of isotopes to reference isotope from each isotope of target element for detection in third standard solution, and $c_{blank}$: Concentration of blank sample for checking measurement procedure.

Hereinafter, exemplary embodiments of the present invention will be described in detail. However, the following examples are only the preferred examples of the present invention and therefore, the present invention is not limited thereto the following examples.

Example 1

Preparation of Target Sample for Detection

As target samples for detection used in the present invention, acrylonitrile butadiene styrene (ABS) samples each containing bromine (Br) with different concentrations were prepared by selection among certified reference materials manufactured by the Korea Research Institute of Standards and Science (KRISS).

Bromine (Br) has two kinds of stable isotopes $^{79}Br=50.69\%$, $^{81}Br=49.31\%$ in natural abundance ratio, and $^{79}Br$ was selected as the reference isotope and $^{81}Br$ was selected as the enriched isotope. Enriched isotope solutions of $^{81}Br$ (Batch No. LM-139201, $^{81}Br=99.62\%$, ORNL, USA) containing a large amount of the enriched isotopes in order to have isotope abundance ratios of Br, such as $^{79}Br=0.38\%$ and $^{81}Br=99.62\%$, and concentration of Br as 2092.541 mg/kg were used to prepare second standard solutions. The prepared target samples for detection were as follows:

1. sample-L: 113-01-012 (# of certified standard material by KRISS, concentration of Br: 25.7 mg/kg)
2. sample-M: 113-01-013 (# of certified standard material by KRISS, concentration of Br: 124.4 mg/kg)
3. sample-H: 113-01-014 (# of certified standard material by KRISS, concentration of Br: 392.0 mg/kg)

Example 2

Preparation of Second Standard Solution

Preparation of the second standard solution, 250 mg/kg $^{81}Br$ 1.19472 (1.19803) g of the $^{81}Br$ enriched isotope solution (2092.541 mg/kg) was diluted with deionized water (D.I. water) to have a final volume of 10.0 (10.00253) g.

Example 3

Preparation of Third Standard Solution

Preparation of the third standard solution, 10 mg/kg Br 1 (1.00054) g of Br (1000.467 mg/kg) was diluted with deionized water (D.I. water) to have a final volume of 100 (99.99769) g.

Example 4

Measurement of Isotope Ratio between Reference Isotope and Enriched Isotope of each of Target Sample for Detection, Second Standard Solution and Third Standard Solution ICP-MS was performed on each of the prepared target sample for detection, the second standard solution, and the third standard solution, to measure isotope ratios (reference isotope/enriched isotope) between the reference isotope and the enriched isotope.

Example 5

Preparation of Second Mixed Solution second mixed solution of sample-L: 0.10 g of the sample-L and 0.02 g of 250 mg/kg $^{81}Br$ were added to prepare a second mixed solution.

second mixed solution of sample-M: 0.03 g of the sample-M and 0.03 g of 250 mg/kg $^{81}Br$ were added to prepare a second mixed solution.

second mixed solution of sample-H: 0.01 g of the sample-H and 0.03 g of 250 mg/kg $^{81}Br$ were added to prepare a second mixed solution.

Example 6

Preparation of Third Mixed Solution third mixed solution-1 (0.1678 mg/kg>0.4947 mg/kg)
1.678 (1.68281) g of 10 mg/kg Br (third standard solution) and 0.134 (0.13426) g of 250 mg/kg $^{81}Br$ (second standard solution) were added, followed by dilution with D.I. water, to prepare a third mixed solution having a final volume of 100 (100.07499) g.

third mixed solution-2 (0.244 mg/kg>0.734 mg/kg)

2.44 (2.45748) g of 10 mg/kg Br (third standard solution) and 0.195 (0.19477) g of 250 mg/kg $^{81}$Br (second standard solution) were added, followed by dilution with D.I. water, to prepare a third mixed solution having a final volume of 100 (100.07941) g.

third mixed solution-3 (0.256 mg/kg>0.779 mg/kg)

2.56 (2.57905) g of 10 mg/kg Br (third standard solution) and 0.205 (0.20587) g of 250 mg/kg $^{81}$Br (second standard solution) were added, followed by dilution with D.I. water, to prepare a third mixed solution having a final volume of 100 (100.03351) g.

Example 7

Measurement of Isotope Ratio between Reference Isotope and Enriched Isotope by Ion Chromatography After Combustion Pretreatment on Each of Second Mixed Solution and Third Mixed Solution The combustion pretreatment process is performed on each of the second mixed solution and the third mixed solution by a combustion pretreatment system, and ICP-MS is then performed thereon, to measure the isotope ratios (reference isotope/enriched isotope) between the reference isotope and the enriched isotope.

Here, an apparatus for the combustion pretreatment process is configured to include three parts of an auto sampler (ASC-240S, Mitsubishi, Japan), a combustion unit including a combustion furnace (AQF-2100H, Mitsubishi, Japan), and an absorption unit including an absorbance system (GA-210, Mitsubishi, Japan) as shown in FIG. 1. When a sample boat containing the target sample for detection and the enriched isotope is mounted by the auto sampler, the sample boat is automatically transferred to a quartz tube of a combustion furnace according to previously input program, and then a combustion process is started. Combustion conditions for the combustion pretreatment process were shown in Table 1 below.

TABLE 1

Combustion Conditions for Combustion Pretreatment Process

| Parameter | part | set value |
|---|---|---|
| Furnace temperature | Inlet | 900° C. |
| | Outlet | 1000° C. |
| Gas flow | Ar | 200 mL/min |
| | O$_2$ | 400 mL/min |
| Ar replace time | | 30 sec |
| Valve selection time | Valve selection ON (OFF) | 1 sec |
| | Ar to O$_2$ valve selection | 10 sec |
| | O$_2$ to Ar valve selection | 10 sec |
| Absorbent solution | H$_2$O$_2$ | 900 mg/kg, 10 mL |

After the combustion pretreatment process as described above, the ICP-MS was performed to measure the isotope ratios (reference isotope/enriched isotope) between the reference isotope and the enriched isotope, wherein the isotope ratios of $^{79}$Br and $^{81}$Br were measured at high resolution with about 10,000 by using Element 2 (Thermo Scientific Inc., Germany), respectively. The measurement conditions of ICP/MS used for experiment were shown in Table 2. When measuring the isotope abundance ratio of bromine, a sample introduction apparatus on the basis of a nebulizer was used wherein since memory effect may be large, a spraying process of distilled water was performed from the auto sampler to the nebulizer, the spray chamber, and the injector, for 2 minutes or more, between the measurement of the sample.

Example 8

Calculation of Concentration of Target Element (Bromine) for Detection Contained in Target Sample for Detection, using the Measured Isotope Ratios Concentration of the target element for detection contained in the target sample for detection was calculated by introducing the isotope ratios of $^{79}$Br and $^{81}$Br in each sample, measured by Examples 1 to 7, into Equation 2 below. Results thereof were shown in Table 2.

$$c_x = c_v \times \frac{m_u m_v}{w \times m_x m'_u} \times \frac{R_u - R_{b'}}{R_{b'} - R_x} \times \frac{R_{b''} - R_v}{R_u - R_{b''}} \times \frac{\sum R_{xi}}{\sum R_{vi}} - c_{blank} \quad \text{[Equation 2]}$$

In Equation 2 above, subscript x is a target sample for detection, subscript u is a second standard solution, subscript v is a third standard solution, subscript b' is a second mixed solution, and subscript b" is a third mixed solution, $c_x$: Concentration of element contained in target sample for detection, $c_v$: Concentration of element contained in third standard solution, $m_x$: Mass of target sample for detection, $m_u$: Mass of second standard solution added together with target sample for detection for preparation of second mixed solution, $m_v$: Mass of third standard solution used for preparation of third mixed solution, $m'_u$: Mass of second standard solution added together with third standard solution for preparation of third mixed solution, w: Dry mass correction factor, $R_x$: Isotope ratio between reference isotope and enriched isotope of target element for detection in target sample for detection, $R_u$: Isotope ratio between reference isotope and enriched isotope of second standard solution, $R_v$: Isotope ratio between reference isotope and enriched isotope of third standard solution, $R_{b'}$: Isotope ratio between reference isotope and enriched isotope of second mixed solution, $R_{b''}$: Isotope ratio between reference isotope and enriched isotope of third mixed solution, $\sum R_{xi}$: Sum of abundance ratios of isotopes to reference isotope from each isotope of target element for detection in target sample for detection $\sum R_{vi}$: Sum of abundance ratios of isotopes to reference isotope from each isotope of target element for detection in third standard solution, and $c_{blank}$: Concentration of blank sample for checking measurement procedure.

Bromine contents in three kinds of plastics measured as measured above were summarized in Table 2 below. Measurement results were shown as standard deviation of measurement values.

Comparative Example 1

Concentration of Br contained in each of the sample-L, the sample-M, and the sample-H prepared as the target samples for detection was measured by a general method of instrumental neutron activation analysis (INAA). Results thereof were shown in Table 2. The measurement results were shown as measurement uncertainty.

Comparative Example 2

Concentration of Br contained in each of the sample-L, the sample-M, and the sample-H prepared as the target samples for detection was measured by the general method of "Standard Test Method for Halogen (F, Cl, Br) and Sulfur Content by Oxidative Pyrohydrolytic Combustion followed by Ion Chromatography Detection" (CIC) established by the Korea Industrial Standard (KS) for bromine analysis in electrical and electronic equipment. Results thereof were shown in Table 2. The calculation procedure of the measurement uncertainty was not established, such that standard deviation for measurements by three times was also shown in the measurement results.

TABLE 2

Measurement results of Example 8 and Comparative Examples 1 and 2

|  | Example 8 (mg/kg) | Standard Deviation (mg/kg) | Comparative Example 1 (mg/kg) | Uncertainty (mg/kg) | Comparative Example 2 (mg/kg) | Uncertainty (mg/kg) |
| --- | --- | --- | --- | --- | --- | --- |
| Sample-L (113-01-012) | 26.02 | 0.16 | 25.7 | 0.64 | 25.60 | 0.2 |
| Sample-M (113-01-013) | 125.1 | 0.46 | 124.4 | 5.7 | 127.8 | 2.4 |
| Sample-H (113-01-014) | 387 | 11 | 392 | 13 | 385.4 | 2.6 |

Figure 2:
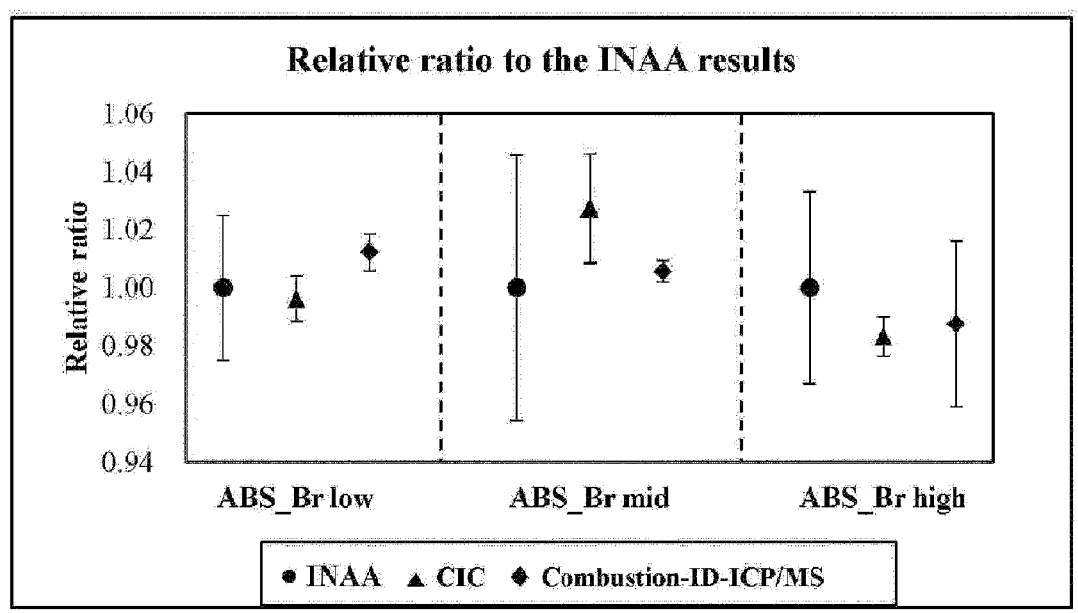
FIG. 2 is a graph showing comparison in measurement reliability between Example 8 and Comparative Examples 1 and 2.
Figure 3:
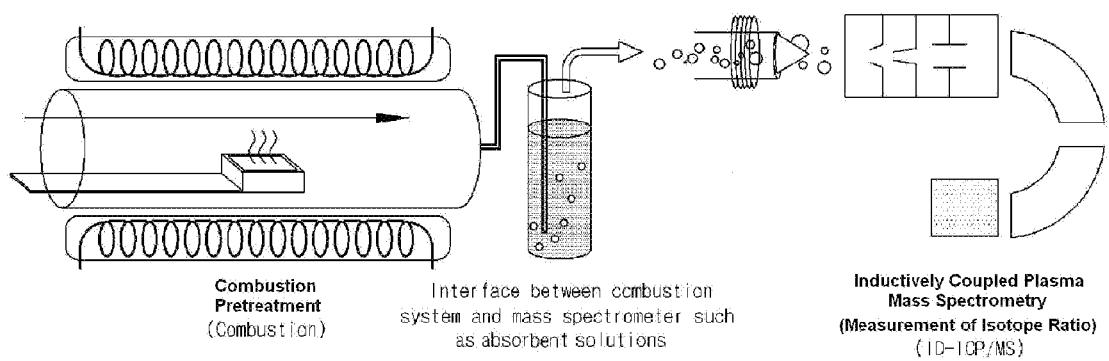
FIG. 3 is a conceptual diagram showing a combustion pretreatment-isotope dilution inductively coupled plasma mass spectrometry (combustion-ID-ICP/MS).

The results of the combustion-ID-ICP/MS according to Example 8 were compared with the results of the INAA according to Comparative Example 1 and the Korea Industrial Standard (KS) for bromine analysis (CIC) according to Comparative Example 2, and the comparison results were relatively shown in FIG. 2. The INAA is known as a method in which when analyzing an element content in the sample in view of measurement, distortion or deviation of the results is rarely shown and relatively small measurement uncertainty is provided, which provides the most excellent reliability. Accordingly, the INAA is a method which is recognized as the top level measurement in Authoritative International Organization of Consultative Committee on the Quantity of Material (CCQM) of the International Bureau on Weights and Measures (BIPM), together with the isotope dilution inductively coupled plasma mass spectrometry. The INNA does not require sample pretreatment, which is significantly appropriate for evaluating a method in which the combustion pretreatment method is coupled with the isotope dilution inductively coupled plasma mass spectrometry, developed by the present inventors. Therefore, on the same sample, the results obtained by the top level measurement, INAA, were compared with the results obtained by the combustion-ID-ICP/MS which is being developed as the top level measurement, through the present research.

In addition, the CIC is a method established as Korea Industrial Standard (KS) for bromine analysis in electrical and electronic equipment, wherein bromine is detected by performing oxidative pyrohydrolytic combustion on a sample and using ion chromatography. The CIC method is not usable as the top level measurement determining certified values of certified standard material, and even in a case in which rigorous analysis such as review of effectiveness, and the like, is required, it is difficult to be used; however, when it is attempted to perform analysis of bromine in the sample taken from the electrical and electronic equipments in general analytical laboratories, the CIC method is generally used. Therefore, on the same sample, the results obtained by CIC were compared with the results obtained by the combustion-ID-ICP/MS which is being developed as the top level measurement, through the present research.

As a result for comparison, the bromine contents in the same ABS sample by three test methods were not different from each other. Accordingly, it could be confirmed that the combustion-ID-ICP/MS developed by the present invention is the top level measurement method which shows comparable results as the INAA. In addition, it could be confirmed that a more accurate method is capable of being provided by substituting the CIC, which is a general method, used in general analytical laboratories. The present invention has an advantage in that significantly excellent analysis results which are the same as those of the INAA are capable of being provided by introducing the combustion pretreatment into the inductively coupled plasma mass spectrometry which is easily usable even in general analytical laboratories as compared to the INAA requiring a neutron source such as a nuclear reactor. In addition, the present invention is an excellent method capable of overcoming disadvantages of the general inductively coupled plasma mass spectrometry using the existing other pretreatments, such as difficulty in obtaining reliability and poor reproducibility due to loss and pollution during the pretreatment.

The invention claimed is:

1. A combustion pretreatment-isotope dilution mass spectrometry measuring concentration of a target element for detection contained in a target sample for detection by using an isotope dilution inductively coupled plasma mass spectrometry, the combustion pretreatment-isotope dilution mass spectrometry, comprising: pretreating the target sample for detection by combustion during an isotope dilution mass spectrometry.

2. The combustion pretreatment-isotope dilution mass spectrometry of claim 1, comprising:
performing an inductively coupled plasma-mass spectrometry on a first standard solution containing a reference isotope and an enriched isotope each at a predetermined amount, the reference isotope and the enriched isotope being isotopes of the target element for detection, to measure a first isotope ratio between the reference isotope and the enriched isotope of the first standard solution;
performing an inductively coupled plasma-mass spectrometry on a combusted material obtained by combusting the target sample for detection to measure a second isotope ratio between a reference isotope and an enriched isotope contained in the target sample for detection;

performing an inductively coupled plasma-mass spectrometry on a combusted material obtained by combusting a first mixed solution prepared by uniformly mixing the first standard solution with the target sample for detection to measure a third isotope ratio between a reference isotope and an enriched isotope contained in the first mixed solution; and calculating concentration of the target element for detection contained in the target sample for detection by using the first, second, and third isotope ratios.

3. The combustion pretreatment-isotope dilution mass spectrometry of claim 2, wherein the combustion of each of the target sample for detection and the first mixed solution is a pretreatment process of performing complete combustion at 900° C. to 1200° C. for 10 minutes to 60 minutes to obtain the combusted material.

4. The combustion pretreatment-isotope dilution mass spectrometry of claim 3, wherein the pretreatment process includes injecting an additive for complete combustion, collecting the combusted material in an absorbent solution, and adsorption-removing an organic material.

5. The combustion pretreatment-isotope dilution mass spectrometry of claim 4, wherein the additive for complete combustion is one or two or more selected from the group consisting of vanadium oxide, iron oxide, permanganate, chromate, osmium tetroxide, and perchlorate.

6. The combustion pretreatment-isotope dilution mass spectrometry of claim 4, wherein the absorbent solution is one or two or more selected from the group consisting of deionized water, sodium hydroxide, tetramethylammonium hydroxide, ammonium carbonate, and hydrogen peroxide.

7. The combustion pretreatment-isotope dilution mass spectrometry of claim 4, wherein the adsorption-removing of the organic material is a step of removing the organic material by using one or two or more adsorbents selected from the group consisting of deionized water, sodium hydroxide, tetramethylammonium hydroxide, ammonium carbonate, and hydrogen peroxide.

8. The combustion pretreatment-isotope dilution mass spectrometry of claim 1, wherein the target element for detection is any one or two or more selected from the group consisting of Cl, Br, Cd, Pb, Hg, Se, Li, B, Mg, Si, S, K, Ca, Ti, V, Cr, Fe, Ni, Cu, Zn, Ga, Ge, Rb, Sr, Zr, Mo, Ru, Pd, Ag, In, Sn, Sb, Te, Cs, Ba, Ce, Nd, Sm, Eu, Gd, Dy, Er, Yb, Hf, Ta, W, Re, Os, Ir, Pt, Tl, and U.

9. The combustion pretreatment-isotope dilution mass spectrometry of claim 1, comprising:

performing an inductively coupled plasma-mass spectrometry on a second standard solution containing a reference isotope and an enriched isotope each at a predetermined amount, the reference isotope and the enriched isotope being isotopes of the target element for detection; and on a third standard solution containing a reference isotope and an enriched isotope each at a predetermined amount at a concentration which is different from that of the second standard solution, the reference isotope and the enriched isotope being isotopes of the target element for detection, to measure a fourth and fifth isotope ratio between the reference isotope and the enriched isotope, of each of the second standard solution and the third standard solution;

performing an inductively coupled plasma-mass spectrometry on a combusted material obtained by combusting the target sample for detection to measure a sixth isotope ratio between a reference isotope and an enriched isotope contained in the target sample for detection;

performing an inductively coupled plasma-mass spectrometry on a combusted material obtained by combusting a second mixed solution prepared by uniformly mixing the second standard solution with the target sample for detection, and on a combusted material obtained by combusting a third mixed solution prepared by uniformly mixing the third standard solution with the second standard solution, to measure a seventh and eighth ratio between a reference isotope and an enriched isotope contained in each of the second mixed solution and the third mixed solution; and calculating concentration of the target element for detection contained in the target sample for detection by using the fourth, fifth, sixth, seventh, and eighth isotope ratios.

10. The combustion pretreatment-isotope dilution mass spectrometry of claim 9, wherein the combustion of each of the target sample for detection, the second mixed solution, and the third mixed solution is a pretreatment process of performing complete combustion at 900° C. to 1200° C. for 10 minutes to 60 minutes to obtain the combusted material.

11. The combustion pretreatment-isotope dilution mass spectrometry of claim 10, wherein the pretreatment process includes injecting an additive for complete combustion, collecting the combusted material in an absorbent solution, and adsorption-removing an organic material.

12. The combustion pretreatment-isotope dilution mass spectrometry of claim 11, wherein the additive for complete combustion is one or two or more selected from the group consisting of vanadium oxide, iron oxide, permanganate, chromate, osmium tetroxide, and perchlorate.

13. The combustion pretreatment-isotope dilution mass spectrometry of claim 11, wherein the absorbent solution is one or two or more selected from the group consisting of deionized water, sodium hydroxide, tetramethylammonium hydroxide, ammonium carbonate, and hydrogen peroxide.

14. The combustion pretreatment-isotope dilution mass spectrometry of claim 11, wherein the adsorption-removing of the organic material is a step of removing the organic material by using one or two or more adsorbents selected from the group consisting of deionized water, sodium hydroxide, tetramethylammonium hydroxide, ammonium carbonate, and hydrogen peroxide.

* * * * *